ical Titrations," South African Journal of Chemistry, 42(3), pp. 96-98 (1989).

(12) United States Patent
Schickaneder et al.

(10) Patent No.: US 9,447,120 B2
(45) Date of Patent: Sep. 20, 2016

(54) CRYSTALLINE FORMS OF ZINC TRISODIUM PENTETIC ACID

(71) Applicant: Hameln Pharma Plus GmbH, Hameln (DE)

(72) Inventors: Christian Schickaneder, Lauf a.d.P. (DE); Vendel Smahovský, Pezinok (SK); Pavol Valachovic, Pezinok (SK); Mathias Dewald, Hameln (DE); Pavel Hradil, Hlusovice (CZ); Janka Králová, Modra (SK); Radek Melnický, Sternberk (CZ); Petr Slézar, Olomouc (CZ); Ivan Kakalik, Senkvice (SK)

(73) Assignee: Hameln Pharma Plus GmbH, Hameln (DE)

( * ) Notice: Subject to any disclaimer, the term of this patent is extended or adjusted under 35 U.S.C. 154(b) by 0 days.

(21) Appl. No.: 14/893,385

(22) PCT Filed: May 23, 2014

(86) PCT No.: PCT/EP2014/060600
§ 371 (c)(1),
(2) Date: Nov. 23, 2015

(87) PCT Pub. No.: WO2014/187930
PCT Pub. Date: Nov. 27, 2014

(65) Prior Publication Data
US 2016/0130283 A1  May 12, 2016

Related U.S. Application Data

(60) Provisional application No. 61/826,507, filed on May 23, 2013.

(30) Foreign Application Priority Data

May 23, 2013  (EP) ..................................... 13168851

(51) Int. Cl.
| | | |
|---|---|---|
| *C07F 3/06* | (2006.01) | |
| *C07F 3/00* | (2006.01) | |
| *A61K 33/30* | (2006.01) | |
| *A61K 49/20* | (2006.01) | |

(52) U.S. Cl.
CPC ................. *C07F 3/06* (2013.01); *A61K 33/30* (2013.01); *A61K 49/20* (2013.01); *C07F 3/003* (2013.01)

(58) Field of Classification Search
None
See application file for complete search history.

(56) References Cited

U.S. PATENT DOCUMENTS 3,480,715 A * 11/1969 Catsch ..................... A61K 8/44
514/587

FOREIGN PATENT DOCUMENTS

GB         1205094    *  9/1970

OTHER PUBLICATIONS

Van der Walt et al., South African Journal of Chemistry (1989), 42(3), 96-8.*
van der Walt et al., "Preparation of CaNa₃DTPA and ZnNa₃ DTPA for (Radio) Pharmaceutical Use. Determination of the DTPA and Calcium or Zinc Contents of the Compounds by Complexometric Titrations," South African Journal of Chemistry, 42(3), pp. 96-98 (1989).

* cited by examiner

*Primary Examiner* — Karl J Puttlitz
(74) *Attorney, Agent, or Firm* — Occhiuti & Rohlicek LLP

(57) ABSTRACT

The invention relates to the production of zinc trisodium pentetic acid (Zn-DTPA) and to new crystalline forms of said salt.

12 Claims, 1 Drawing Sheet

CRYSTALLINE FORMS OF ZINC TRISODIUM PENTETIC ACID

CROSS-REFERENCE TO RELATED APPLICATIONS

This application is the national phase under 35 USC 371 of International Application No. PCT/EP2014/060600, filed May 23, 2014, which claims the benefit of the priority dates of European Application No. 13168851.7, filed May 23, 2013 and U.S. Provisional Application No. 61/826,507, filed May 23, 2013. The contents of the aforementioned applications are incorporated herein in their entirety.

The present invention relates to the preparation of trisodium zinc diethylenetriaminepentaacetate (Zn-DTPA) (Formula (I)) and crystalline forms of this salt.

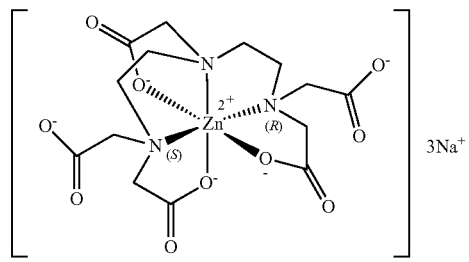

Formula (1)

The invention relates further to the use of trisodium zinc diethylenetriaminepentaacetate as a medicament and particularly a formulation orally administrable to humans and/or animals comprising the said compound. The invention also relates to the use of Zn-DTPA or an oral formulation comprising this compound for the treatment or prophylaxis of poisoning with heavy metals and/or radionuclides.

BACKGROUND OF THE INVENTION

Diethylenetriaminepentaacetic acid (DTPA) is a chelating agent. Chelating agents are used as standard in industry since they form stable complexes with metals, to some extent selectively. In the pharmaceutical industry, diethylenetriaminepentaacetic acid is used in the form of a calcium or zinc complex. These complexes are able to exchange the cation for another cation if this cation has a higher complex formation constant, i.e. forms a stable complex with the complexing agent. Solutions of these salts are used in Europe and in the USA for the complexation of radionuclides. (Ménétrier F, Grappin L, Raynaud P, Courtay C, Wood R, Joussineau S, List V, Stradling G N, Taylor D M, Bérard P, Morcillo M A & Rencova J (2005) Treatment of accidental intakes of plutonium and americium: Guidance notes. Appl Radiat Isot, 62: 829-846.)

Finished drug products with Zn-DTPA are registered under the trade names pentetate zinc trisodium (USA, NDA August 2004, hameln pharmaceuticals) and zinc trisodium pentetate (DE, Heyl Chemisch-pharmazeutische Fabrik GmbH & Co.).

The drug products are administered by intravenous injection. They are indicated for a nuclear incident in which radioactive heavy metals, such as plutonium, americium and curium have been released. Guilmette, R. A. et al "Effectiveness of continuously infused DTPA therapy in reducing the radiation dose from inhaled 244Cm2O3 aerosols" Health Physics, 1992. vol. 62, no. 4, pp. 311-318.

Efforts are also currently being undertaken to increase the oral bioavailability of the complex (WO 2007/145682).

For the intravenous dosage forms, the formation of the zinc complex in solution is a satisfactory synthetic route. However, the use for oral administration places higher demands on the physical properties of the active ingredient. The complex must be present in solid form. It should preferably be in a stable state that is easy to handle.

The synthesis of the active ingredient was first published in DE1223396 (Example 1). The standard method for preparing Zn-DTPA consists in providing an aqueous solution of pentasodium diethylenetriaminepentaacetate and the addition of zinc chloride or zinc oxide, according to the following scheme:

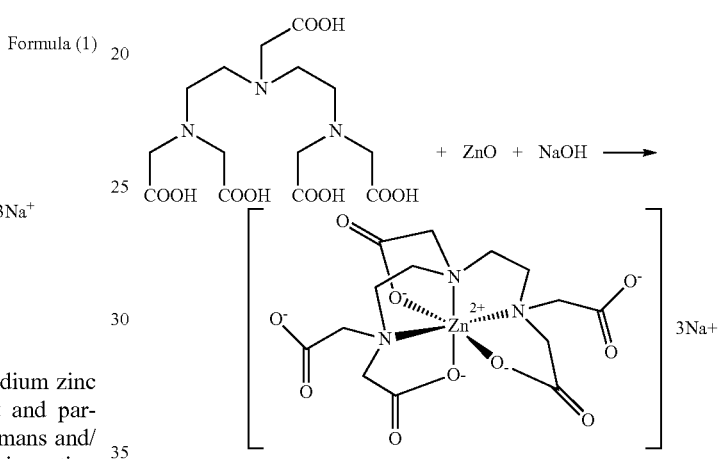

In this case, the isolation of the active ingredient is achieved via concentration of the reaction solution by distilling off the water and subsequent drying of the reaction product. The synthetic route presented in DE 1223396, however, leads to an amorphous product, which is very hygroscopic and accordingly difficult to grind.

In an application from Nanotherapeutics, the hygroscopy is also presented as a disadvantageous property of Zn-DTPA (WO 2007008480, Example 4). It is reported that the lyophilized powder, absorbs more than 10% by weight of water over 24 h. DE1223396 gives no indication of the existence of a crystalline form, or different polymorphic forms of Zn-DTPA.

Table 1 shows the hygroscopy of the solid when the product is obtained by the route known from the prior art by concentration of the reaction mixture (cf. also Example 1).

TABLE 1

| Time [h] | Mean mass increase [%] | | | | | |
|---|---|---|---|---|---|---|
| No. | 1 | 2 | 4 | 6 | 8 | 24 | 48 |
| Batch 1 | 0.51 | 0.89 | 1.56 | 2.35 | 2.95 | 7.38 | 11.92 |
| Batch 2 | 0.56 | 0.97 | 1.73 | 2.61 | 3.26 | 7.82 | 12.02 |

The mass increase due to hygroscopy after 12 hours is about 7-8%, and the mass increase of the sample after 48 hours is about 12%. This is around the value known from the prior art for Zn-DTPA. The hygroscopy of conventional Zn-DTPA is so great that, with sufficiently long exposure to air humidity, it even deliquesces due to its hygroscopy.

Ca-DTPA forms a similar complex due to the comparable electron configuration of calcium (Ca: [Ar]4s2; Zn:[Ar]3d10 4s2). However, the complex is distinctly more unstable due to the different atom radii. A comparison of the two complexes in terms of their chemical and physical properties is therefore problematic.

To prepare Ca-DTPA, a method is described in which an alcohol is added to a cold aqueous solution of the product in order to effect a precipitation (GB944020). A crystalline form of this complex is however also not described here.

It has not been possible to date to prepare Zn-DTPA in a form which leads to a stable product that can be processed to an oral pharmaceutical dosage form under atmospheric conditions.

Against this background, it was the object of the present invention to provide Zn-DTPA in a form which is more stable under atmospheric conditions than the form known and preparable to date. In particular, it was the object of the invention to retard and/or reduce the hygroscopy of Zn-DTPA. In addition, the DTPA according to the invention should preferably be suitable for oral pharmaceutical dosage forms.

This object is achieved by trisodium zinc diethylenetriaminepentaacetate (Zn-DTPA) in crystalline form.

SUMMARY OF THE INVENTION

If any doubt about the definition of the word "crystalline" should exist, then "crystalline" is understood to mean, in the context of this text, that ions or molecules are not randomly arranged in the corresponding substance but are arranged regularly in a crystal structure. This is revealed in the X-ray diffractogram by a distinctly recognizable diffraction pattern. Examples of such diffraction patterns are given in the Figures. The reflections shown therein, such as presented in Tables 1 and 2 for example, are reproducible for each crystal form arranged at the same 2 theta angle. As already described above, crystalline forms of Zn-DTPA have not been accessible to date. It has been shown, surprisingly, that such crystalline forms can be prepared by the method further described below. It has been shown, particularly surprisingly, that the hygroscopicity is retarded and reduced overall in the crystalline forms. For this purpose, reference is also made to the embodiments further given below.

Trisodium zinc diethylenetriaminepentaacetate according to the invention preferably exists in a crystalline form of which the X-ray powder diffractogram can be assigned to an X-ray powder diffractogram having at least the following characteristic peaks (Form I, FIG. 1):

TABLE 2

| Pos. [°2Th.] | d-spacing [Å] | Rel. Int. [%] |
|---|---|---|
| 6.8836 | 14.90 | 48 |
| 8.1807 | 12.54 | 100 |
| 14.477 | 7.10 | 52 |
| 17.725 | 5.81 | 43 | or having at least the following characteristic peaks (Form II, FIG. 2):

TABLE 3

| Pos. [°2Th.] | d-spacing [Å] | Rel. Int. [%] |
|---|---|---|
| 11.302 | 9.08 | 21 |
| 14.892 | 6.90 | 32 |

TABLE 3-continued

| Pos. [°2Th.] | d-spacing [Å] | Rel. Int. [%] |
|---|---|---|
| 16.699 | 6.16 | 100 |
| 21.721 | 4.75 | 41 |

Figure 1:
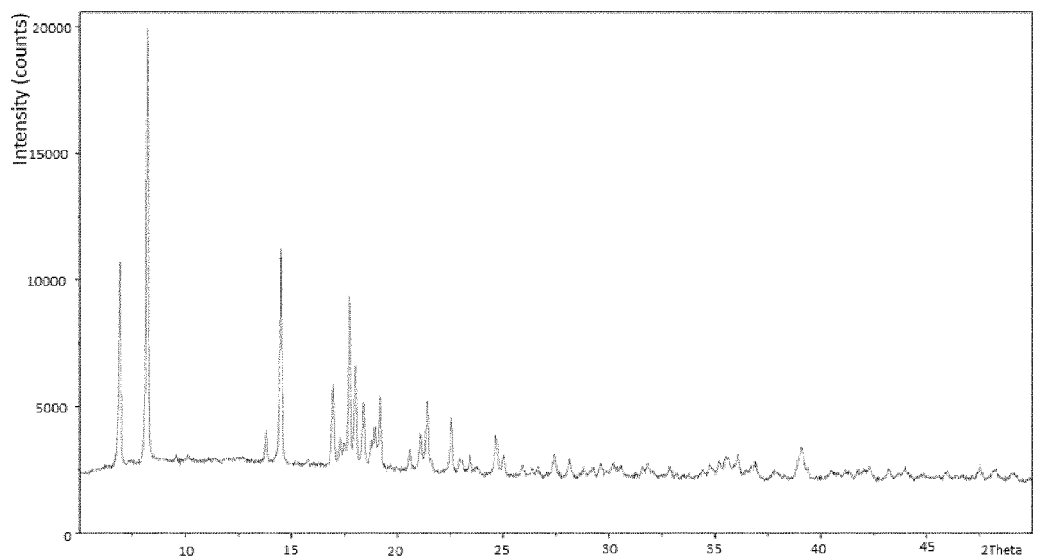
FIG. 1 is an X-ray powder diffractogram of Form I of trisodium zinc diethylenetriaminepentaacetate according to the invention.
Figure 2:
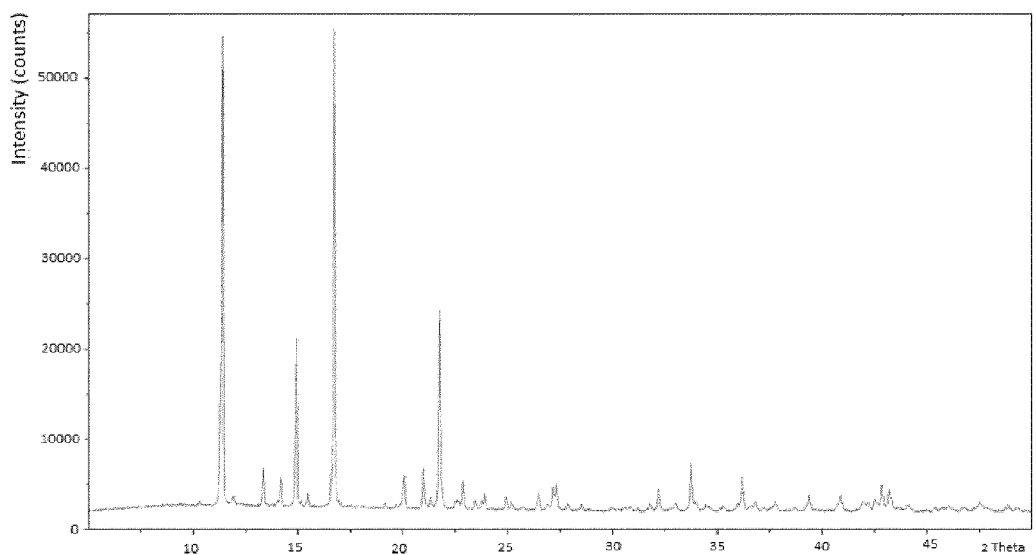
FIG. 2 is an X-ray powder diffractogram of Form II of trisodium zinc diethylenetriaminepentaacetate according to the invention.

The X-ray diffractograms in FIG. 1 and FIG. 2 show the two crystalline forms I and II. Unless otherwise stated, the X-ray diffractogram data in this text refers to recordings which were made with Co K-alpha radiation. A precise description of the X-ray diffractogram recordings can be found in Example 7.

DETAILED DESCRIPTION

Here, it is clear to those skilled in the art that—depending on the very specific measurement conditions—it can lead to deviations which relates to the peak position and the relative intensity of the peaks. Accordingly, in the context of this text, an "X-ray powder diffractogram which can be assigned to an X-ray powder diffractogram having a certain peak position and peak intensity" signifies that those skilled in the art are able to state that the measured sample corresponds to the particular peak pattern and the corresponding peak intensities taking into account the particular measurement situation. This signifies that the diffraction pattern is essentially in agreement with the Figures of the preferred crystal form, preferably that the peaks of the X-ray powder diffractogram of the preferred crystal forms according to the invention are in each case shifted by at most ±0.5, particularly preferably ±0.3 with respect to their position, preferably with respect to their d value, from the data given in this text. In particular, the intensities stated in the Tables are for information only and are not to be regarded as limiting for the inventive crystal form in this context.

Form I is produced, for example, when methanol is used to precipitate Zn-DTPA from a hot, aqueous solution. See also Example 2.

Trisodium zinc diethylenetriaminepentaacetate according to the invention preferably exists in a crystalline form of which the X-ray powder diffractogram can be assigned to an X-ray powder diffractogram, that exhibits at least one or even all the peaks given in the following Table in addition to the peaks in Table 3, in the X-ray powder diffractogram of the crystalline form of Zn-DTPA according to the invention (Form I, FIG. 1).

TABLE 4

Peak list (Form I)

| Pos. [°2Th.] | d-spacing [Å] | Rel. Int. [%] |
|---|---|---|
| 6.8836 | 14.90 | 48 |
| 8.1807 | 12.54 | 100 |
| 13.781 | 7.46 | 7 |
| 14.477 | 7.10 | 52 |
| 17.725 | 5.81 | 43 |
| 20.567 | 5.01 | 4 |

Form II is produced, for example, when water is removed from the reaction mixture by azeotropic distillation with n-butanol (see, e.g. Example 5 below), and the product is crystallized out from the reaction mixture. A more complete peak list for Form II is shown below (Table 5), wherein it is preferred that, as well as the peaks specified above, at least one, two, three or even all peaks additionally specified in the following Table are found in the X-ray powder diffractogram of the crystalline form of Zn-DTPA according to the invention.

TABLE 5

Peak list (Form II)

| Pos. [°2Th.] | d-spacing [Å] | Rel. Int. [%] |
|---|---|---|
| 11.302 | 9.08 | 21 |
| 11.384 | 9.02 | 86 |
| 14.892 | 6.90 | 32 |
| 16.699 | 6.16 | 100 |
| 20.038 | 5.14 | 6 |
| 20.962 | 4.92 | 8 |
| 21.721 | 4.75 | 41 |
| 22.840 | 4.52 | 6 |
| 26.436 | 3.91 | 3 |
| 27.139 | 3.81 | 4 |
| 27.291 | 3.79 | 5 |
| 28.494 | 3.63 | 1 |
| 32.168 | 3.23 | 5 |
| 33.734 | 3.08 | 10 |
| 34.426 | 3.02 | 1 |
| 36.161 | 2.88 | 8 |
| 36.777 | 2.84 | 2 |
| 42.811 | 2.45 | 6 |
| 43.183 | 2.43 | 5 |

The crystalline forms of Zn-DTPA (particularly those preferred) according to the invention are also characterized by high chemical stability and low hygroscopicity. Here, the Zn-DTPA according to the invention is superior to the products known from the prior art, not only with respect to its absolute hygroscopicity but also with respect to the rate of water absorption.

Accordingly, trisodium zinc diethylenetriaminepentaacetate according to the invention is preferred, wherein the trisodium zinc diethylenetriaminepentaacetate, starting from a water content of 8% by weight, absorbs ≤10% by weight of water on storage at 65% air humidity and 25° C. for 48 h.

Preference is given to trisodium zinc diethylenetriaminepentaacetate according to the invention, which, starting from a water content of 8% by weight, absorbs ≤7% by weight of water on storage at 65% air humidity and 25° C. for 48 h.

A slower rate of water uptake in particular has the advantage that fewer rigid measures are required with respect to reduced air humidity in the processing of the crystalline form of Zn-DTPA according to the invention, and in the ideal case, the forms according to the invention can be processed to, for example, pharmaceutical formulations even without particular measures.

The following Table 6 shows the comparison between conventionally prepared amorphous Zn-DTPA and two inventive crystalline forms. Here, the samples used were each subjected to the same pre-drying process (cf. Examples 3 and 4). The samples were exposed in each case for the time period stated in the Table at 25° C. and an air humidity of 65% relative air humidity.

Table 6 shows the comparison between conventionally prepared amorphous Zn-DTPA and the two crystalline forms.

TABLE 6

| | Mean mass increase [%] | | | | | | |
|---|---|---|---|---|---|---|---|
| Time [h] No. | 1 | 2 | 4 | 6 | 8 | 24 | 48 |
| Form I (from Example 2) | 0.32 | 0.54 | 0.92 | 1.34 | 1.64 | 3.91 | 6.81 |
| Form II, A (from Example 3) | 0.34 | 0.57 | 1.00 | 1.49 | 1.84 | 4.42 | 5.07 |
| Form II, B (from Example 4) | 0.41 | 0.72 | 1.29 | 1.97 | 2.43 | 5.18 | 5.25 |
| Amorph I (from Example 1) | 0.51 | 0.89 | 1.56 | 2.35 | 2.95 | 7.38 | 11.92 |
| Amorph II (from Example 1) | 0.56 | 0.97 | 1.73 | 2.61 | 3.26 | 7.82 | 12.02 |

The crystalline forms according to the invention thus show a mass increase of less than 10%, preferably less than 7%, particularly preferably less than 6% after 48 hours under the stated conditions.

The absolute water uptake of the crystalline forms according to the invention is also distinctly improved compared to the amorphous forms known from the prior art. The latter even have a tendency to deliquesce on sufficiently long exposure to air humidity. Accordingly, an inventive trisodium zinc diethylenetriaminepentaacetate according to the invention is preferred, wherein this remains in the solid state on storage at 65% air humidity and 25° C. for 200 h.

Further preference is given to an inventive trisodium zinc diethylenetriaminepentaacetate which, on storage at 65% air humidity and 25° C. for 200 h, comprises a total content of ≤16% by weight, preferably ≤15% by weight, more preferably ≤14% by weight of water.

The advantage of the lower hygroscopicity (absolute) particularly lies in the fact that the crystalline forms according to the invention reliably remain as solids, while the amorphous forms of Zn-DTPA known from the prior art even tend to deliquesce. The forms according to the invention thereby open up a series of further applications.

Accordingly, a part of the invention is trisodium zinc diethylenetriaminepentaacetate according to the invention for use as a medicament. As already described above, the crystalline forms have not been accessible to date and accordingly—despite an existing need—could not be used in the medicinal field.

Against this background, and particularly in view of the improved properties (especially in relation to the hygroscopicity), part of the invention is, in particular, a pharmaceutical formulation orally administrable to humans and/or animals comprising Zn-DTPA in accordance with the invention.

A variety of practical formulations, particularly for oral and especially as a pharmaceutical administration are potentially useful owing to the improved stability of the Zn-DTPA according to the invention. An orally administrable formulation in this case is a formulation which can be administered to an animal or a human, particularly to a human, due to its constituents, and preferably also due to its consistency. A pharmaceutical formulation is in the context, a formulation that preferably meets the requirements imposed on pharmaceutical products, particularly in Germany.

The orally administrable, particularly orally administrable pharmaceutical formulation is preferably a solid formulation comprising a suitable carrier. The solid formulation may be achieved by direct compression of the active ingredient or may comprise further aids selected from the group consisting of fillers, in particular starch (corn, potato or wheat starch), lactose, glucose, mannitol or sorbitol; binders, in particular MCC (microcrystalline cellulose) or starch; wet binders/adhesives for granulation, in particular starch paste, cellulose ethers, Kollidon or gelatins; disintegrants, especially potato starch, corn starch, PVP, Carbopol or magnesium peroxide and lubricants.

This part of the invention is also the use of Zn-DTPA according to the invention or an orally administrable formulation comprising Zn-DTPA according to the invention for the treatment or prophylaxis of poisoning with heavy metals and/or radionuclides. Here, radionuclides in particular are the preferred type of application. In this case, the Zn-DTPA according to the invention or the formulation comprising this is particularly effective with regard to heavy metals and/or radionuclides selected from the group consisting of uranium, curium, plutonium and americium, wherein the latter two mentioned are particularly preferred.

Part of the invention is a process for preparing trisodium zinc diethylenetriaminepentaacetate comprising the steps of:
 a) reacting diethylenetriaminepentaacetic acid with zinc oxide or another zinc salt in the presence of water,
 b) concentrating the reaction solution twice to ≤15% of the starting volume and subsequent addition of an organic solvent and
 c) isolating the crystalline reaction product.

Using this method according to the invention, in particular Form I described above can be distinctively prepared.

Part of the invention is also a method for preparing trisodium zinc diethylenetriaminepentaacetate according to the invention comprising the steps of:
 a) reacting diethylenetriaminepentaacetic acid with zinc oxide or another zinc salt in the presence of water,
 b) removing 90-99% by weight, preferably 94 to 96% by weight of the water from the reaction mixture, wherein 15 to 100% by weight, preferably 20-60% by weight, particularly preferably 20 to 45% by weight of organic solvent, based on the water content before the start of the water removal, is added in parallel or before starting the water removal,
 c) optionally adding further organic solvent after step b),
 d) further removing water and preferably also organic solvent until the steam temperature is in the range of ±5° C. of the boiling temperature of the organic solvent and/or until crystallization occurs and
 e) isolating the crystalline reaction product.

This method according to the invention is particularly suitable for the preparation of crystalline form II.

In general, the Zn-DTPA according to the invention can be prepared by neutralization of diethylenetriaminepentaacetic acid in aqueous solution by sodium hydroxide and subsequent addition of zinc oxide. Other zinc salts besides zinc oxide are also possible.

For the method according to the invention, it is particularly advantageous if the (organic) solvent is selected such that the solubility of Zn-DTPA in the solvent is less than 1 g/ml. Since the product according to the invention is highly soluble in water, the water must be removed from the reaction mixture during the preparation of the product according to the invention (see above).

It is possible in principle to remove water, for example, by vacuum distillation before which or during which a suitable solvent should be added in order to replace part of the water. As has been described above, it is preferred that 15-100% by weight, preferably 20-45% by weight of organic solvent are added as said solvent, based on the water content before starting removal of the water.

The products according to the invention are particularly reliably obtained if it is checked how much volume of water has been removed from the reaction solution. This is possible, for example, by collecting the water, however, as an alternative, the distillation temperature is a good indication of the remaining water content in the reaction mixture.

In this context, azeotropic distillation is a particularly suitable method of water removal, in which the water is removed stepwise and the remaining proportion of water in the reaction mixture is inversely proportional to the temperature.

Azeotropic distillation is a common method for the removal of water from an oily reaction product; see also EP1413575, Example 5. Toluene is selected as agent. A further example for the removal of water from a reaction product by azeotropic distillation is described in EP0449445.

Accordingly, it is advantageous if the (organic) solvent used forms an azeotrope with water. Thus, the removal of the water via azeotropic distillation is facilitated, wherein water is removed from the reaction mixture until the product can start to crystallize in the heat. It is also possible in this case, after reaching the preferred water content of only about 1-10% by weight, preferably 4-6% by weight of the water originally present or particularly preferably of about 5% by weight of the original water present, to add organic solvent once again.

In addition, it may be preferable in accordance with the invention to recycle the organic solvent back into the reaction solution during the azeotropic distillation. It may also be preferable in this context, after removal of the water, also to distill off organic solvent in connection with the azeotropic distillation.

As a general rule, the water and optionally organic solvent are distilled until a honey-like liquid results, which preferably precipitates on the reactor surface and becomes more dense with increasing removal of water.

In preferred embodiments of the method according to the invention, the product begins to solidify at 97-98° C. steam temperature.

By way of preference, on reaching a steam temperature of 110° C. (particularly in the context of an azeotropic distillation using n-butanol, as organic solvent), the crystalline product according to the invention precipitates.

This is preferably now isolated by a filtration step.

The organic solvents to be used for the method according to the invention are preferably selected from the group consisting of acetone, n-butanol, 2-methyl-1-propanol, methanol, ethanol, n-propanol, 2-propanol, 2-methyl-2-propanol, toluene and ethyl acetate.

With particular preference, methanol is the organic solvent for the preparation of crystal form I, whereas particularly preferably toluene, and most preferably n-butanol is the organic solvent to be used for crystalline form II.

However, there is no reason not to use other solvents, which form an azeotrope with water, for the preparation by the method according to the invention. As already indicated above, the removal of water by azeotropic distillation in the method according to the invention is advantageous, but it is not necessary for every solvent. Similar results can also be achieved if the reaction solution is sufficiently concentrated by (any) distillation, and subsequently an (organic) solvent is added to the aqueous reaction solution.

Preferred steps for the method according to the invention are the neutralization of the Diethylenetriaminepentaacetic acid used with a solution of sodium hydroxide and/or cooling of the reaction mixture, in particular, prior to a filtration.

However, since it is possible in principle also to obtain the filtrate from the hot suspension, the isolation of the reaction product according to the invention is relatively as rapid as possible, wherein impurities remain in the liquid filtered off.

Therefore, particularly in the context of the preferred method according to the invention, it is possible to take advantage of two effects: firstly, the low solubility of Zn-DTPA in certain organic solvents and secondly, the ability of certain solvents to form an azeotrope with water, in order to control optimally the conditions of the water removal and the progression of the water removal. These properties have indeed been used before for removing water from reaction mixtures, but it is surprising that, by means of the invention and particularly the preferred methods according to the invention, it is possible to obtain Zn-DTPA in a defined crystalline form with reproducible product properties and reduced hygroscopicity and thus improved stability.

The preferred method according to the invention in the form of the azeotropic distillation has particularly the following advantages:

- it is relatively easy to determine the amount of water remaining in the reaction mixture (due to the temperature proportionality), particularly when compared with other water removal methods such as vacuum distillation for example. Naturally, this applies also to the amount of water removed from the reaction mixture.
- on using the preferred solvent, particularly n-butanol, in connection with an azeotropic distillation, an advantage lies in the low solubility of the product in the solvent, and also in a high reaction yield.
- it is also possible to recover the organic solvent, particularly n-butanol, which reduces the production costs.
- Particularly advantageous in the method according to the invention is that only one polymorphic form is obtained.

EXAMPLES

Example 1

Preparation of Amorphic Zn-DTPA 152.5 g of NaOH were dissolved in 1.7 L of water and the solution was cooled to 30° C.

Subsequently, 500 g of DTPA were added with stirring and the mixture was stirred until a clear solution formed (about 20 min) 103.4 g of zinc oxide were added to the solution and the solution was stirred overnight until a clear solution resulted.

The pH was adjusted to 7.0 with a 10% NaOH solution and the solution filtered. The solution was then concentrated at 40° C. under vacuum with vigorous stirring and dried at 90° C. at 2.5 kPa for 17 hours.

This gave 641.1 g, corresponding to 96.5% of theory. Purity by HPLC: 99.6%; water content: 7.16%.

Example 2

Preparation of Crystalline Zn-DTPA Form I 296 g of NaOH were dissolved in 3.4 L of water and the solution was cooled to 30° C.

Subsequently, 1 kg of DTPA was added with stirring and the mixture was stirred until a clear solution formed (about 20 min) 207 g of zinc oxide were added to the solution and the solution was stirred overnight until a clear solution resulted The pH was adjusted to 7.01 with a 10% NaOH solution and the solution filtered. The solution was then concentrated at 40° C. under vacuum with stirring and 3.2 L of methanol added. The solution was again concentrated such that 3 L of liquid were distilled off. Another 2 L of methanol were added, such that a solid crystallized out. The crystals were filtered off and dried at 90° C. at 2.5 kPa for 17 hours.

This gave 812.4 g, i.e. 61.14% of theory. Purity by HPLC: 99.6%; water content by Karl Fischer: 5.49%.

Example 3

Preparation of Crystalline Zn-DTPA Form II

In an apparatus with water separator, 296 g of NaOH were dissolved in 3.4 L of water and 1 kg of DTPA was added with stirring. 207 g of zinc oxide were added and the pH adjusted to 7.0. 1 L of n-butanol was added to the suspension and the solution heated with removal of water (azeotropic distillation) until crystallization occurred. After cooling of the reaction solution the crystalline product was filtered off.

Drying the product at 90° C. at 2.5 kPa for 17 hours gave 1.3 kg, corresponding to 100% of theory; content by HPLC, 101.6%, water content: 8%.

Example 4

Preparation of Crystalline Zn-DTPA Form II

In an apparatus with water separator, 296 g of NaOH were dissolved in 3.4 L of water and 1 kg of DTPA was added with stirring. 207 g of zinc oxide were added and the pH adjusted to 7.0. About 2.5 L of water were distilled off 1 L of n-butanol was then added to the solution which was heated with removal of water until crystallization occurred. After cooling of the reaction solution the crystalline product was filtered off.

Drying the product at 90° C. at 2.5 kPa for 17 hours gave 1.2 kg, corresponding to 92% of theory; content by HPLC, 100.0%, water content: 7.6%.

Example 5

5 kg of diethylenetriaminepentaacetic acid were added to a solution of 1.48 kg of sodium hydroxide in water (17 kg). 1.04 g of zinc oxide was then added and the reaction mixture was stirred.

As the next step, diatomite (1.0 kg) was added and the suspension filtered through a suitable filter and subsequently washed with water. 22 kg of butanol were now added to the filtrate and this mixture subjected to an azeotropic distillation at atmospheric pressure.

The water was removed during the distillation and the volume of the water removed and also the distillation temperature were regularly checked. The n-butanol phase was fed back into the reaction vessel and, during the azeotropic distillation, a further 6 kg of n-butanol were added stepwise to the reaction mixture in order to partly replace the water removed.

On reaching a temperature of 101-102° C., further n-butanol (12 kg) was added and the distillation continued until a temperature of 110° C. in the reaction mixture was reached. No more n-butanol was fed into the reaction mixture at this point, and all n-butanol was removed.

The boiling suspension was stirred and the reaction product separated by filtration. In this case, it is possible in principle to cool the reaction mixture or to filter it hot.

Finally, the end product was dried in a vacuum drier at 90° C. and the desired product (crystal form II) was obtained.

The remaining liquid, and also the butanol phase could be distilled and the recovered butanol could be used for the next batch.

Example 6

Determination of the Hygroscopicity

The hygroscopicity of Zn-DTPA was checked by measuring the weight increase in a controlled environment. At air temperature (25±2°) C. and (60±5)% air humidity in a stability chamber (Thermo TEC), the weights of two samples (5.000 g) in each case were checked (Analytical balance, XS 205, Mettler Toledo). The weight was checked after 1, 2, 4, 6, 8, 24 and 48 hours.

Example 7

Determination of the X-Ray Powder Diffractogram

The X-ray powder diffractogram pattern of the solid forms of Zn-DTPA were determined over the 2 theta range 2° to 51° on a Bragg Brentano focusing powder diffractometer, Philips, Model 1730/10 (Philips, Holland), where the diffractometer was linked to a PC for further evaluation.

The instrument was equipped with an X-ray radiation tube providing Co Kα radiation of wavelength 0.179021 nm. The measurement conditions were as follows:

Excitation voltage: 40 kV, anode current strength: 35 mA, step size: 0.02°, step time 2.4 seconds.

Sample: smooth surface, inserted into a nickel sample holder. The sample was measured and stored at room temperature. In the measurements, the samples were used as lightly pressed powder discs. Prior to the measurements, the material samples were very gently pestled using an agate mortar and an agate bowl.

The qualitative characteristics of the diffraction pattern, i.e. the peak positions and relative intensities of the samples measured are given (in the whole text) in a Table (d value and intensity and ° 2 theta).

The results of the measurements of the relevant samples are given in FIGS. 1 and 2 and in the Tables above.

The invention claimed is:

1. A trisodium zinc diethylenetriaminepentaacetate (Zn-DTPA) in crystalline form, wherein the X-ray powder diffractogram of the Zn-DTPA can be assigned to an X-ray powder diffractogram having at least the following characteristic peaks (Form II):

| Pos. [°2Th.] | d-spacing [Å] | Rel. Int. [%] |
|---|---|---|
| 11.302 | 9.08 | 21 |
| 14.892 | 6.90 | 32 |
| 16.699 | 6.16 | 100 |
| 21.721 | 4.75 | 41. |

2. The trisodium zinc diethylenetriaminepentaacetate as claimed in claim 1, wherein the trisodium zinc diethylenetriaminepentaacetate, starting from a water content of 8% by weight, absorbs ≤10% by weight of water on storage at 65% air humidity and 25° C. for 48 h.

3. The trisodium zinc diethylenetriaminepentaacetate as claimed in claim 1, wherein the trisodium zinc diethylenetriaminepentaacetate, starting from a water content of 8% by weight, absorbs ≤7% by weight of water on storage at 65% air humidity and 25° C. for 48 h.

4. The trisodium zinc diethylenetriaminepentaacetate as claimed in claim 1, wherein the trisodium zinc diethylenetriaminepentaacetate remains in the solid state on storage at 65% air humidity and 25° C. for 200 h.

5. The trisodium zinc diethylenetriaminepentaacetate as claimed in claim 1, wherein the trisodium zinc diethylenetriaminepentaacetate comprises ≤16% by weight of water on storage at 65% air humidity and 25° C. for 200 h.

6. The trisodium zinc diethylenetriaminepentaacetate as claimed in claim 1, wherein the trisodium zinc diethylenetriaminepentaacetate comprises ≤14% by weight of water on storage at 65% air humidity and 25° C. for 200 h.

7. A pharmaceutical formulation comprising the trisodium zinc diethylenetriaminepentaacetate as claimed in claim 1.

8. The pharmaceutical formulation of claim 7, wherein the formulation is orally administrable to an animal.

9. A method of treating an animal for poisoning with heavy metals and/or radionuclides, wherein the method comprises administering the pharmaceutical formulation of claim 8 to the animal.

10. A method for preparing trisodium zinc diethylenetriaminepentaacetate as claimed in claim 1, comprising the steps of:
    a) reacting diethylenetriaminepentaacetic acid with zinc oxide or another zinc salt in the presence of water,
    b) removing 90 to 99% by weight of the water from the reaction mixture by azeotropic distillation, wherein 15 to 100% by weight n-butanol, based on the water content before the start of the water removal, is added in parallel or before starting the water removal;
    c) optionally adding further organic solvent after step b),
    d) further removing water until the steam temperature is in the range of ±5° C. of the boiling temperature of the organic solvent and/or until crystallization occurs and
    e) isolating the crystalline reaction product.

11. The pharmaceutical formulation of claim 8, wherein the animal is a human.

12. The method of claim 9, wherein the animal is a human.

* * * * *